United States Patent [19]
Vidlund

[11] Patent Number: 6,110,164
[45] Date of Patent: *Aug. 29, 2000

[54] GUIDELESS CATHETER SEGMENT

[75] Inventor: Robert M. Vidlund, Maplewood, Minn.

[73] Assignee: Intratherapeutics, Inc., St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/985,834

[22] Filed: Dec. 5, 1997

[51] Int. Cl.$^7$ ................................. A61M 25/00
[52] U.S. Cl. .................... 604/524; 604/525; 604/526; 604/527; 604/530
[58] Field of Search ............................ 604/264, 95, 523, 604/524, 526, 530, 532; 600/585, 435

[56] References Cited

U.S. PATENT DOCUMENTS

| | | |
|---|---|---|
| 3,169,528 | 2/1965 | Knox, III et al. . |
| 4,516,972 | 5/1985 | Samson . |
| 5,095,915 | 3/1992 | Engelson . |
| 5,176,660 | 1/1993 | Truckai .................................. 604/282 |
| 5,178,158 | 1/1993 | de Toledo . |
| 5,222,949 | 6/1993 | Kaldany .................................. 604/282 |
| 5,364,357 | 11/1994 | Aase . |
| 5,368,049 | 11/1994 | Raman et al. .......................... 128/772 |
| 5,380,304 | 1/1995 | Parker . |
| 5,454,795 | 10/1995 | Samson . |
| 5,507,751 | 4/1996 | Goode et al. . |
| 5,507,766 | 4/1996 | Kugo et al. . |
| 5,569,200 | 10/1996 | Umeno et al. . |
| 5,573,520 | 11/1996 | Schwartz et al. . |
| 5,599,326 | 2/1997 | Carter . |
| 5,601,539 | 2/1997 | Corso, Jr. ............................... 604/282 |
| 5,658,264 | 8/1997 | Samson . |
| 5,662,622 | 9/1997 | Gore et al. ............................. 604/282 |
| 5,685,841 | 11/1997 | Mackool . |

FOREIGN PATENT DOCUMENTS

| | | |
|---|---|---|
| 0 554 722 A1 | 8/1993 | European Pat. Off. . |
| 0 790 066 A2 | 8/1997 | European Pat. Off. . |
| 0 808 637 A2 | 11/1997 | European Pat. Off. . |
| 90 13 331 | 12/1990 | Germany . |
| PCT/US96/ 08232 | 5/1996 | WIPO . |

*Primary Examiner*—Wynn Wood Coggins
*Assistant Examiner*—Deborah Blyvers
*Attorney, Agent, or Firm*—Merchant & Gould P.C.

[57] ABSTRACT

A catheter includes a segment having a longitudinal axis. The segment includes a polymeric tube having interior and exterior surfaces separated by a wall thickness. The interior surface defines a catheter lumen which extends coaxially with the longitudinal axis. The exterior surface is sized for the tube to be passed through a patient's vasculature system. The segment further includes a substantially straight, flexible guide member disposed within the tube's wall thickness. The guide member has a longitudinal dimension extending parallel to and radially spaced from the segment's axis. The guide member is plastically deformable when bent around a bending axis perpendicular to the longitudinal dimension beyond a bending limit.

9 Claims, 5 Drawing Sheets

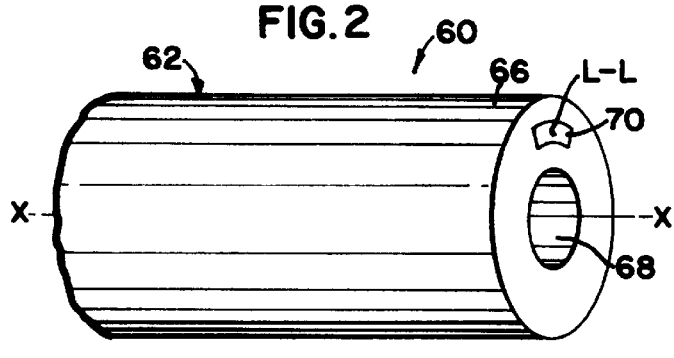
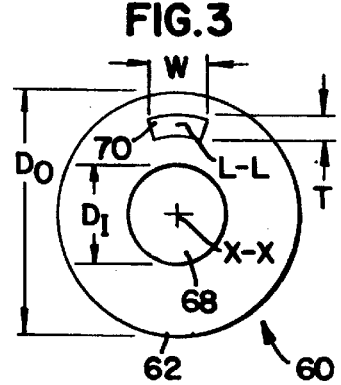
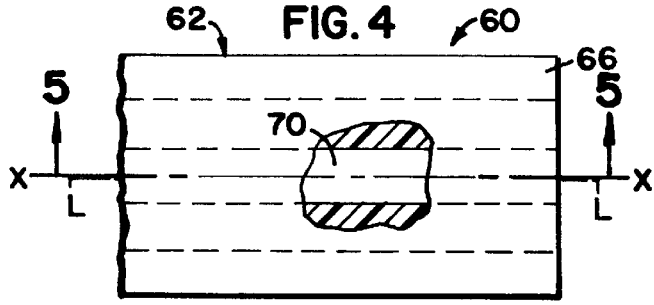
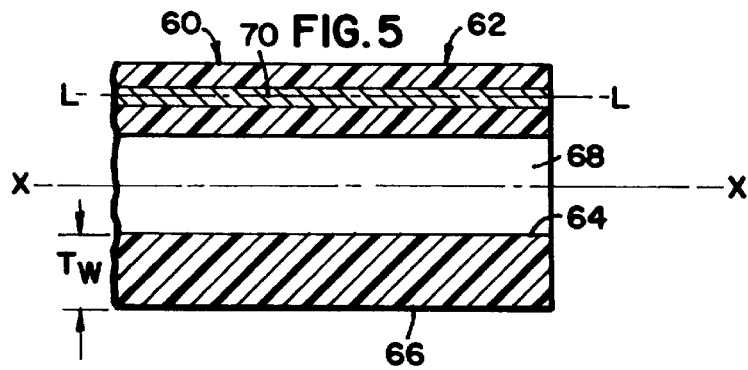
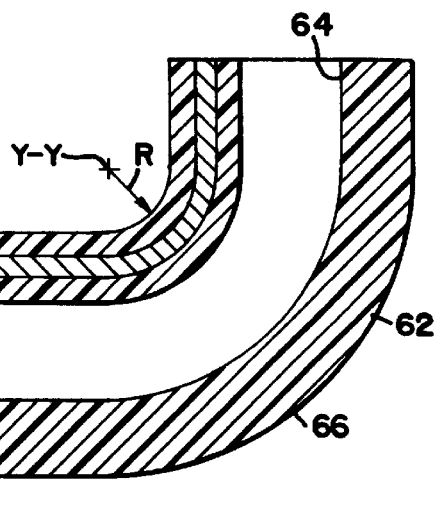

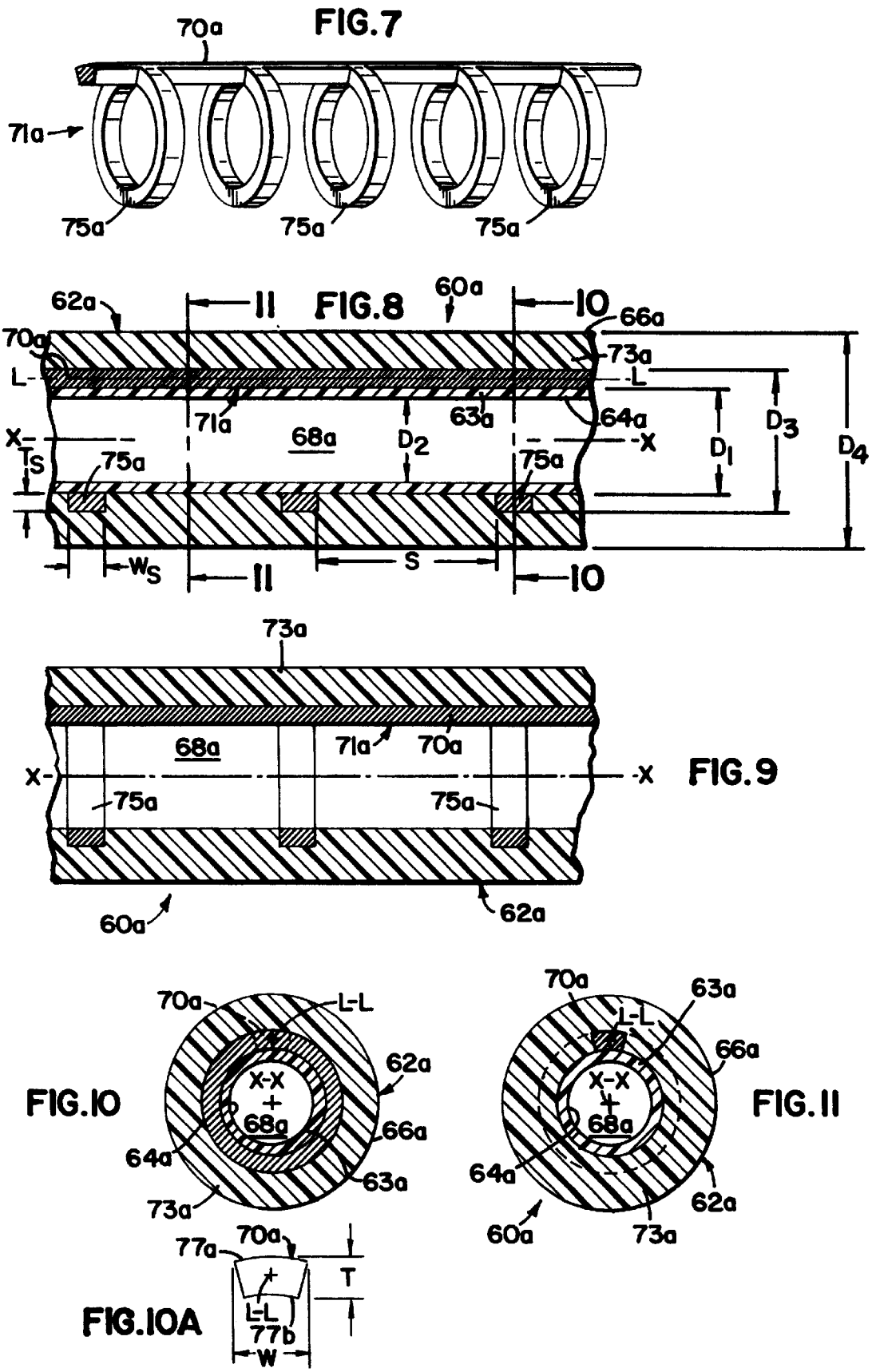

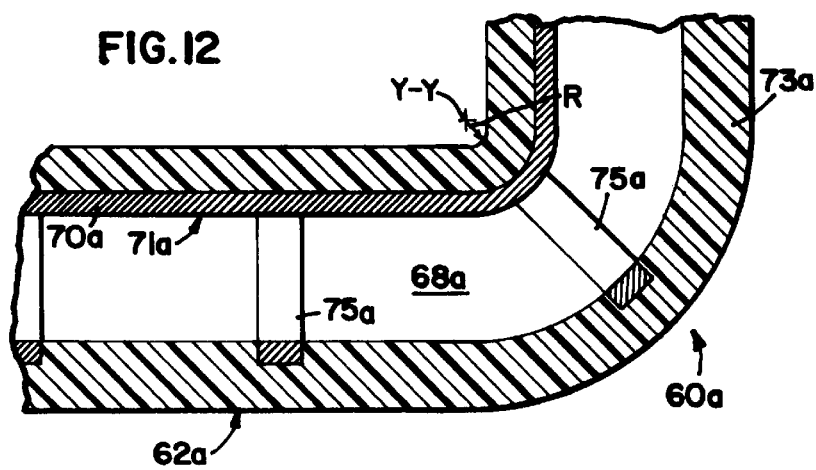
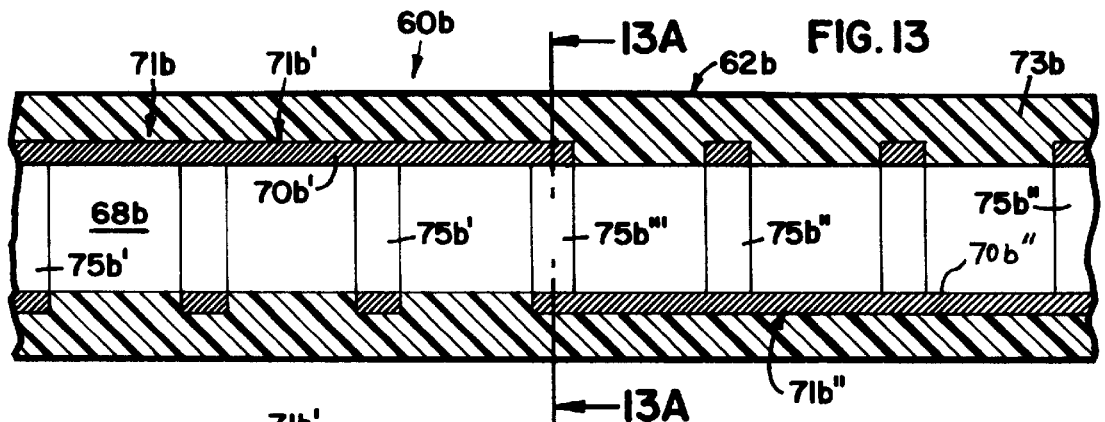
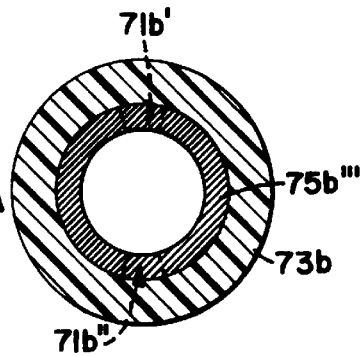
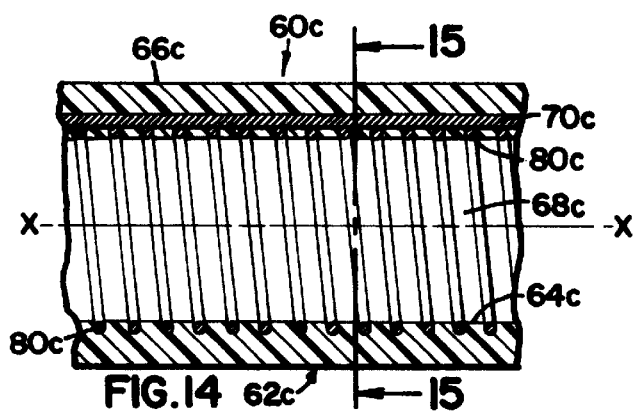
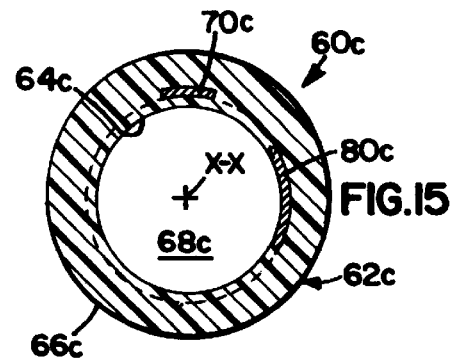

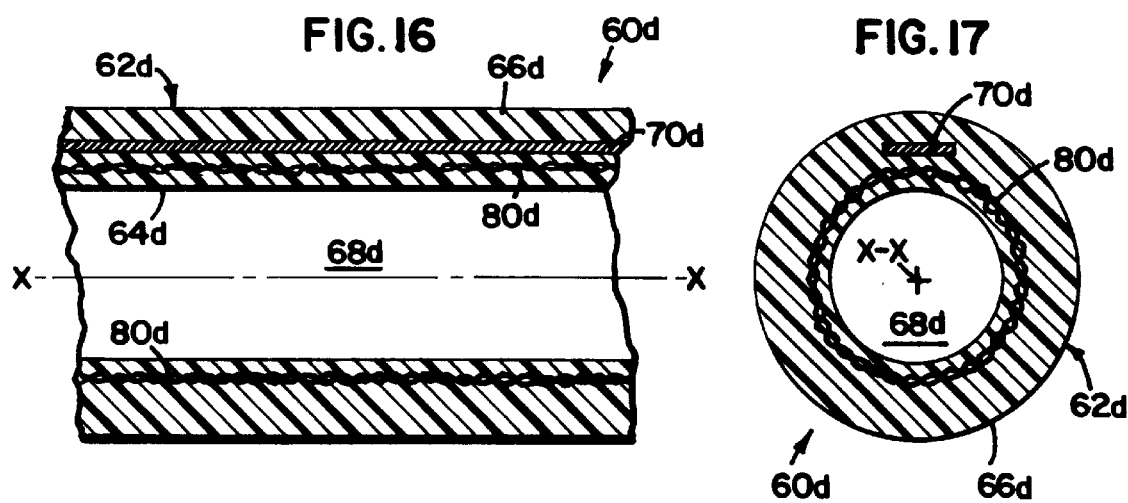

GUIDELESS CATHETER SEGMENT

BACKGROUND OF THE INVENTION

1. Field of the Invention

This invention pertains to catheters for passage through a vasculature system. More particularly, this invention pertains to a novel construction of at least a segment of a catheter.

2. Description of the Prior Art

Catheters are widely used in medical treatment. A catheter is an elongated flexible member advanced through the vasculature system to a desired site. The catheter may be advanced over a previously inserted guide wire. Some catheter designs permit use without a guide wire. In such designs, the catheter flows through the vasculature (referred to as "flow directed" catheters).

With the catheter in place, a wide variety of substances may be passed through the catheter to the site. For example, drugs may be moved through the catheter for site-specific drug delivery. Also, implements may be passed through the catheter. The catheter may also be used to remove fluids from the site. Still further, a catheter may be equipped with implements (e.g., balloon tips) for performing procedures (e.g., angioplasty) at the site.

Catheters have long been used in cardiovascular treatment. More recently, catheters are used in neurological procedures requiring advancement of the catheter through very narrow vessels. To accomplish these advances, a high degree of flexibility is desired. Also, catheters need very thin walls in order to retain an internal bore having as large a diameter as possible.

In neurological applications, catheters preferably have extremely flexible distal tips. While a high degree of flexibility is desired, flexibility should be attained while retaining burst strength and without undue sacrifice of torque transmission response.

In certain applications, the distal tip of a catheter may be shaped for unique purposes. For example, in treating an aneurysm, the distal tip may be shaped to have a radial projection so the tip more easily enters and remains in the aneurysm upon reaching the site. A common practice is to shape the tip through steam application. The steam application softens the polymer material at the tip permitting it to be bent and retain a bent shape following the steam application. Where the distal tip is supported by a traditional coil or braid construction, the tip may not adequately retain the bent shape since the coil or braid is inclined to resume its unbent shape against the resistance of the polymer. For example, in response to body temperature, the tip may relax during use in a procedure.

In prior catheters used for neurological purposes, guide wires are used to position the catheter. Such guide wires include a deformable tip. The physician bends the tip as desired to facilitate accurate advancement of the tip. Guide wire tips can be bent without the aforementioned problems associated with bent-tip catheters since there is no coil or braid which is inclined to return the guide wire tip to its pre-bent shape.

It is also desirable to eliminate the need for guide wires. While some catheter designs may be usable without guide wires, many physicians opt to use guide wires with such catheters. Guide wires add costs, procedure steps and risks. By enhancing catheter designs to operate without the need for guide wires, physicians are more inclined to use catheters in such manner.

SUMMARY OF THE INVENTION

According to a preferred embodiment of the present invention, a catheter is disclosed including a segment having a longitudinal axis. The segment includes a polymeric tube having interior and exterior surfaces separated by a wall thickness. The interior surface defines a catheter lumen extending coaxially with the longitudinal axis. The exterior surface is sized for the tube to be passed through a patient's vasculature system. The segment further includes a substantially straight, flexible guide member disposed within the tube's wall thickness. The guide member has a longitudinal dimension extending parallel to and radially spaced from the segment's axis. The guide member is plastically deformable when bent beyond a bending limit around a bending axis perpendicular to the longitudinal dimension.

BRIEF DESCRIPTION OF THE DRAWINGS

FIG. 2 is a perspective view of a segment of the catheter of FIG. 1;

FIG. 3 is an end sectional view of the segment of FIG. 2;

FIG. 4 is a top plan view of the segment of FIG. 2 with a guide member shown in phantom lines;

FIG. 5 is a cross-sectional, longitudinal view of the segment of FIG. 4 taken along line 5—5 in FIG. 4;

FIG. 6 is the view of FIG. 5 following a bending of the segment of FIG. 5 about a bending axis;

FIG. 7 is a perspective view of a support structure according to an alternative embodiment of the present invention;

FIG. 8 is a cross-sectional, longitudinal view of a longitudinal segment of the catheter of FIG. 1 incorporating the support structure of FIG. 7;

FIG. 9 is the view of FIG. 8 with an inner liner removed to expose circumferential supports and guide member according to the present invention and to expose an outer liner;

FIG. 10 is a view taken along line 10—10 of FIG. 8;

FIG. 10A is an enlarged, transverse cross-sectional view of the guide member of FIG. 10;

FIG. 11 is a view taken along line 11—11 of FIG. 8;

FIG. 12 is the view of FIG. 9 following a bending of the segment of FIG. 9 about a bending axis;

FIG. 13 is a cross-sectional, longitudinal view of a longitudinal segment of the catheter of FIG. 1 incorporating a further alternative embodiment support structure and with an inner liner removed to expose circumferential supports and guide members according to the present invention and to expose an outer liner;

FIG. 13A is a view taken along line 13A—13A of FIG. 13;

FIG. 14 is a cross-sectional, longitudinal view of a longitudinal segment of the catheter of FIG. 1 incorporating a still further alternative embodiment of the present invention;

FIG. 15 is a view taken along line 15—15 of FIG. 14;

FIG. 16 is a cross-sectional, longitudinal view of a longitudinal segment of the catheter of FIG. 1 incorporating a yet further alternative embodiment of the present invention; and FIG. 17 is a view taken along line 17—17 of FIG. 16.

DESCRIPTION OF THE PREFERRED EMBODIMENT

Figure 1:
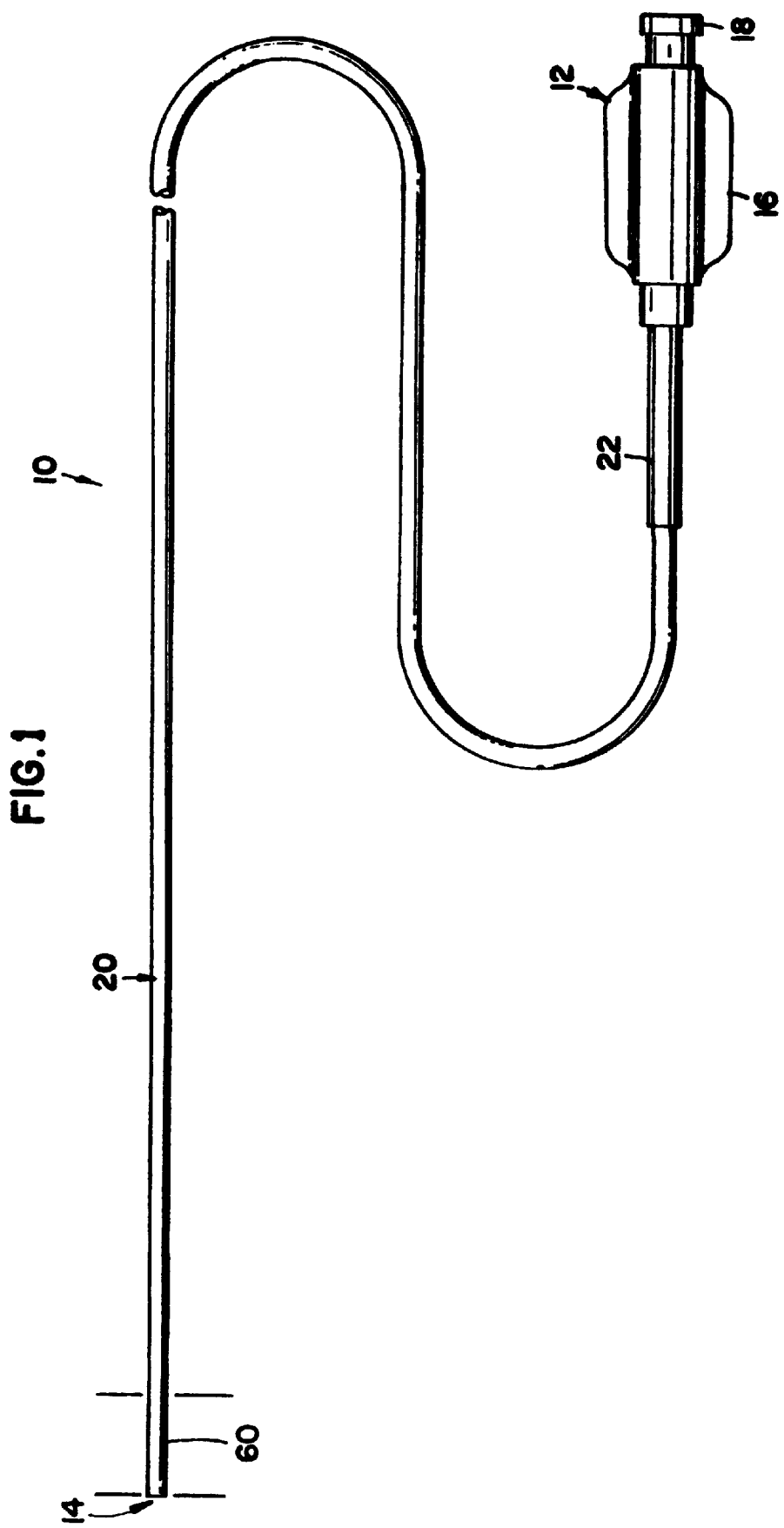
FIG. 1 is an overall view of a catheter according to the present invention.

Referring now to the several drawing figures in which identical elements are numbered identically throughout, a description of a preferred embodiment of the present invention will now be provided.

FIG. 1 illustrates a catheter 10. The catheter 10 extends from a proximal end 12 to a distal end 14. At the proximal end 12, a hub 16 is provided to be gripped by a physician as well as having an inlet 18 for injection of fluids into the catheter 10. A flexible hollow shaft 20 is connected to the hub 16. The shaft 20 is sized to be inserted into a patient's vasculature. The shaft 20 is commonly about 150 cm long. A strain relief jacket 22 connects the shaft 20 to the hub 16. The foregoing description forms no part of this invention and is given to facilitate an understanding of the present invention.

The catheter 10 includes a segment 60 having the novel construction of the present invention. (For purposes of the remainder of this description, the word "catheter" is generally used to refer to the flexible shaft 20 of FIG. 1 having the segment 60 which a construction as will be described.) While the entire length of the catheter 10 can be constructed as will be described with reference to segment 60, it may be desirable to have a catheter 10 of multiple segments of different construction to impart different properties to different regions of the catheter 10 along its length. For example, it may be desirable to provide a catheter 10 having a proximal portion stiffer than a more flexible distal portion. While the present invention is suitable for forming catheter segments of varying degrees of flexibility and other properties, the present invention is described with reference to a segment 60 of the length of the catheter 10. This is to allow for catheters where the entire length is constructed according to the teachings of this application as well as catheters where only a discrete portion is so constructed and where the remainder is constructed according to conventional catheter construction techniques.

With reference to FIGS. 2–6, a first embodiment of segment 60 is shown. Segment 60 includes a flexible, polymeric tube 62. The tube 62 may be any suitable flexible material for use in the vascular system. Such materials may be nylon or urethane. The tube 62 has an interior surface 64 and an exterior surface 66 separated by a wall thickness $T_W$ (FIG. 5). The interior surface 64 defines a catheter lumen 68 having a longitudinal axis X—X. The diameter $D_O$ of the exterior surface 66 is sized for the tube 62 to be passed through the vasculature of a patient. By way of non-limiting examples, $D_O$ may be 0.74 mm and the diameter $D_I$ of lumen 68 may be 0.53 mm resulting in a wall thickness $T_W$ of 0.10 mm.

A substantially straight, flexible guide member 70 is disposed within the wall thickness $T_W$ embedded within the material of tube 62. The guide member 70 has a central longitudinal dimension (or axis) L—L extending parallel to and radially spaced from the axis X—X. While guide member 70 could be circular in cross-section, the guide member 70 preferably has a width W greater than a thickness T. The width W is measured perpendicular to a radial line from the axis X—X to the longitudinal dimension L—L of the guide member 70. The thickness T is measured perpendicular to both the longitudinal dimension L—L and the width W. The width W is greater than the thickness T. By way of non-limiting representative example, the width W is about 0.13 mm and the thickness T is about 0.03 mm. The length of the guide member 70 may be the entire length of the segment 60 (which may be the entire length of the catheter but in a preferred embodiment will be the final distal portion of the catheter 10, about 5 cm, as will be described).

The guide member 70 is plastically deformable when bent around a bending axis spaced from and perpendicular to the longitudinal dimension L—L. For example, with reference to FIG. 6, the segment 60 is bent about a bending axis Y—Y by a radius R. When bent beyond a bending limit, the guide member 70 is plastically deformed and retains its bent shape. When bent below the bending limit, the guide member 70 remains flexible and elastically is urged to a straight shape as shown in FIG. 5. The segment 60 is bent such that the bending axis Y—Y is on the same side of axis X—X as guide member 70. The amount of bending varies with materials and such calculation for a specific material and geometry of the guiding member 70 is within ordinary skill in the art. For example, when stainless steel is strained greater than 1%, it is plastically deformed.

Guide member 70 can be any one of a number of materials. Preferably, the guide member 70 is fabricated from medical grade stainless steel. Other possible materials include nickel—titanium alloys (e.g, nitinol) and cobalt—chromium—nickel alloys (e.g, Elgiloy™ alloy of Elgiloy, Inc. of Elgin, Ill., U.S.A.). Other shapeable materials include platinum, plastics, polymers, etc.

With the structure thus shown, a physician can bend a distal tip of a catheter 10 by bending the segment 60 beyond the bending limit. Alternatively, catheter manufacturers can supply catheters with pre-bent tips. The segment 60 retains the bent shape unlike the catheters bent according to the previously described prior art shaping technique (which are inclined to revert to a straight shape for the reasons previously stated). With a tip so formed, the catheter 10 can more easily guide through the vasculature without a guide wire.

For ease of illustration, the invention has been described in an embodiment with a single layer tube 62 with no support structure other than guide member 70. Numerous alternative embodiments are possible to facilitate fabrication, increase burst strength, enhance flexibility, improve torque transmission response and resist kinking. Non-limiting examples of such alternatives will now be described. Elements functionally in common will be numbered identically (and not separately described) with additions of "a", 'b" etc. to the numbering to distinguish between the embodiments.

With reference to FIGS. 7–12, a first alternative embodiment is shown as segment 60a. The segment 60a is a multi-layer construction including a flexible inner layer 63a. By way of non-limiting example, the inner layer 63a is polytetraflouroethylene (PTFE) more commonly known by the trademark Teflon™. In a preferred embodiment, layer 63a has an outer diameter $D_1$ of 0.0230 inch (0.58 mm) and an inner diameter $D_2$ of 0.0210 inch (0.53 mm) to define an internal bore 68a surrounded by the Teflon™ inner tube layer 63a.

The segment 60a also includes a support structure 71a (as will be more fully described and shown separately in FIG. 7). The support structure 71a is generally tubular and is adhered to the external surface of the inner layer 63a by a thin bonding layer of any suitable adhesive (not shown but which may be polyurethane having a thickness of about 0.0004 inch or 0.01 mm). The support structure 71a has an outer diameter $D_3$ of about 0.025 inch (0.635 mm).

Surrounding the exterior of the support structure 71a, an outer polymer jacket 73a is provided. The outer jacket 73a may be any suitable flexible material for use in the vascular system. Such materials may be nylon or urethane. The outer jacket 73a has an outer diameter $D_4$ of 0.029 inch (0.74 mm).

In the foregoing, Applicants have provided a specific description of various layers of segment 60a as well as describing specific materials and dimensions. Such specificity has been given to describe a preferred embodiment of a specific catheter 10 utilizing the novel support structure 71a as will be described. More or fewer layers of materials could be used with structure 71a to impart desired properties (e.g., varying stiffness, strength, etc.) to segment 60a. Similarly, specific materials and dimensions may be varied to alter the properties of segment 60a.

Referring now to FIG. 7, the novel support structure 71a of the present invention will now be described. The support structure 71a includes a plurality of circumferential supports 75a. Each of the supports 75a is a ring coaxially surrounding the axis X—X.

The circumferential supports 75a are positioned in parallel, spaced-apart alignment along axis X—X. Linearly aligned portions of the circumference of the rings 75a are interconnected by a guide member 70a having the dimensions given with respect to guide member 70. Since the rings 75a are only connected along one line (represented by the linear guide member 70a), the segment 60a is highly flexible with the rings 75a providing structural integrity to retain the cross-sectional geometry of bore 68a.

By way of example, the circumferential supports 75 have a width $W_S$ of about 0.003 inch (0.076 mm). The width $W_S$ is the dimension parallel to the axis X—X. The circumferential supports 75a thickness $T_S$ of about 0.001 inch (0.025 mm) (i.e., the same as thickness of the guide member 70a). Finally, the circumferential supports 75a have an axial spacing S between opposing supports 75a of about 0.005 inch (0.127 mm).

Preferably, the support structure 71a is fabricated from a solid blank of medical grade stainless steel hollow tubing. Other possible materials include nickel—titanium alloys (e.g, nitinol) and cobalt—chromium—nickel alloys (e.g., Elgiloy™ alloy of Elgiloy, Inc. of Elgin, Ill., U.S.A.). Such a fabrication process includes starting with a rod (not shown) having an outer diameter equal to the desired inner diameter of the PTFE layer 63a. The PTFE layer 63a is placed over the rod. The rod acts as a jig to hold the elements of catheter 10 during fabrication. The adhesive (not shown) is applied to the external surface of PTFE layer 63a. A solid tube of medical grade stainless steel (referred to as a hypotube) is then adhered to PTFE layer 63a by the adhesive. As an alternative, the PTFE layer 63a and the metal tube can be assembled without the adhesive with parts held in alignment until the final outer layer 73a is applied.

The solid metal tube is then milled to remove excess material of the tube as waste and leaving only the material of the circumferential supports 75a and guide member 70a as the support structure 71a. In a preferred embodiment, the metal tube is milled by a chemical milling process. In such a process, a pattern mask of the desired pattern of the circumferential supports 75a and guide member 71a is placed over the metal tube. A light source sensitizes a photoresist applied to the metal to create a pattern on the metal tube matching the mask. The photo-sensitized tube is then chemically etched to dissolve away the areas of the tube corresponding to the waste leaving only the desired material of the circumferential supports 75a and guide member 71a. It will be appreciated that this description of a chemical milling of the metal tube forms no part of this invention per se. Such a process is more fully described in commonly assigned and copending U.S. patent application Ser. No. 08/645,607 the specification of which was published on Dec. 5, 1996 as International Publication No. WO96/38193 on PCT International application Ser. No. PCT/US96/08232.

After the tube is so milled, the outer layer 73a is applied to the outer surface of the support structure 71a. The material of the outer layer 73a may, at the option of a designer, fill in the axial spacing S between the circumferential supports 75a or leave such spacing as voids to enhance flexibility. The rod is then removed from the PTFE layer 63a leaving a completed segment 60a.

With the fabrication as described, the rings 75a and guide member 70a are solidly connected of the same material and are portions of a cylinder (i.e., the remaining portions of a cylindrical hypotube after the chemical milling process). Such solid connection is not required but is given as an example. For example, the rings 75a could be less than complete rings which are in close tolerance with but not connected to the guide member 70a. This option provides greater flexibility while having the rings 75a and guide member 70a in the same layer.

With the construction shown, guide member 70a is not a true rectangle in cross-section but is substantially rectangular (and has a width W greater than a thickness T). As illustrated in FIG. 10A, the guide member 70a so constructed has arcuate outer and inner surfaces 77a, 77b which conform to the geometry of the tube from which the support 71a is formed. By way of example, outer surface 77a has a radius of 0.32 mm while inner surface 77b has a radius of 0.29 mm.

The circumferential supports 75a increase the burst strength of the catheter 10 when used to infuse drugs or other media at high pressure (i.e., 300 psi). The rings 75a are reinforcing members resisting radial expansion forces urging the catheter toward expansion. Further, the rings 75a resist kinking and other geometric deformation of the internal cross-section of the catheter 10.

The foregoing embodiment has been described in a preferred manner and may be modified while keeping with the teachings of the present invention. For example, the support structure 71a need not be formed of metal or fabricated in the chemical milling manner indicated. The support structure 71a can be formed from any structural material in any manner including, without limitation, electrical discharge machining, laser cutting, or assembly of individual components.

Similarly, while a preferred support structure 71a has been disclosed, numerous modifications can be made to the structure to vary the properties of the catheter 10 to meet design objectives for a specific application. The geometry of the support rings 75a can be varied (e.g, wider, narrower, closer or more distant spacing as well as non-symmetrical shapes compared to the symmetrical shapes shown) to vary strength and flexibility.

FIG. 13 shows an alternative embodiment of the support structure 71a. In FIG. 13, the support structure 71b includes two portions 71b', 71b". Each of portions 71b', 71b" is identical in construction to support 71a. Similar elements are similarly numbered with distinguishing single and double apostrophes and need not be separately described.

In the embodiment of FIG. 13, the guide member 70b' of portion 71b' is circumferentially offset from the guide member 70b" of portion 71b". In the example given, the guide members 70b', 70b" are circumferentially spaced by 180°. As a consequence, the two portions 71b', 71b" may be bent in opposite directions permitting a compound curve to the segment 60b. The two portions are integrally formed as described and interconnected by a common ring 75b'". The shape of the resulting compound bend can be modified by altering the degree of circumferential offset of the guide members 71b', 71b" (e.g, by setting the guide members 71b', 71b" at an offset of 90° instead of 180°).

FIGS. 14–16 illustrate incorporation of the present invention into otherwise conventional catheter designs. FIGS. 14 and 15 show the invention in a segment 60c having a tube 62c containing a coil 80c within the thickness of the tube wall. The tube 62c is shown as a single layer construction for ease of illustration but could be a multi-layer construction.

The coil 80c extends the length of the segment 60c and provides torque transmission response throughout the length. While one coil 80c is shown, consistent with prior known construction, multiple coils could be used e.g., overlying clockwise and counter-clockwise coils).

A guide member 70c according to the present invention is imbedded within the wall thickness of tube 62c. The guide member 70c is shown positioned radially outwardly from coil 80c but could also be positioned radially inwardly. With this construction, the physician can bend the segment as described. While the coil 80c tends to urge the segment to the straight alignment, the plastically deformed guide member 70c is better apply to resist the straightening tendency of the coil 80c than would be a steam bent polymer tube 62c without the guide member 70c.

FIGS. 16–17 illustrate the invention in a segment 60d having a tube 62d containing a braid 80d within the thickness of the tube wall. The braid is a metallic (or other structural material) woven sleeve well-known in the prior art for use in catheter construction. A guide member 70d according to the present invention is also imbedded within the wall thickness of tube 62d. The guide member 70d imparts the previously described benefits to the braid construction.

While FIGS. 14–17 illustrate use of the present invention in prior art construction, such modification is not preferred. For example, the construction of FIGS. 8–12 is preferred over that of FIGS. 14–15 since the rings 75a of FIGS. 8–12 do not impart a straightening force to the bent segment 60a (FIG. 12) unlike the coil 80c of FIG. 14. This permits use of a smaller guide member 70a. Also, it is believed the segment 60a will be more flexible than the segment 60c. Additionally, with the fabrication described with reference to FIGS. 8–12, the guide member 70a resides in the same radial layer as the rings 75a since the guide member 70a and rings 75a are formed from the same hollow tube.

In each of the embodiments of FIGS. 14 and 16, the guide member 80c, 80d is in a different layer than the coil 80c or braid 80d. This results in a thicker wall for tube 62c, 62d. A thin wall is desired to minimize the outside diameter of the segment 60c, 60d (to fit into very small vessels) while maximizing the inside diameter of the bore (to provide less resistance to therapeutic fluids or other matter advanced through the lumen 65c, 65d).

As mentioned, the segment of the present invention is preferably utilized in the most distal portion of a catheter (e.g., the final 3–5 cm). The remainder of the catheter may be of any other construction selected for size, flexibility, torque transmission response or such other design factor which a designer elects to emphasize. An additional option is to provide a further distal tip onto segment 60–60d. Such additional tip will be about 3–5 mm in length and will not be provided with a guide member 70–70d. This enhances flexibility at the tip and cushions any penetrating blow (which might perforate vessels) which an advancing guide member 70–70d may otherwise present to opposing tissue during advancement.

From the foregoing, the present invention has been disclosed in a preferred embodiment. The invention permits construction of a catheter overcoming disadvantages of prior designs as well as providing a structure having various features which can be modified to design catheters with optimum performance for a wide variety of applications. It is intended that modifications and equivalents of the disclosed concepts, such as those which readily occur to one of skill in the art, shall be included within the scope of the claims appended hereto.

What is claimed is:

1. A catheter having a longitudinal axis, said catheter comprising:
   A. a flexible hollow shaft having a distal end and a proximal end, said distal end sized to be inserted into a patient's body lumen;
   B. said shaft including at least a segment having:
      (a) a polymeric tube having interior and exterior surfaces separated by a wall thickness, said interior surface defining a catheter lumen extending coaxially with said longitudinal axis, said exterior surface sized for said tube to be passed through the vasculature of a patient;
      (b) at least a first substantially straight, flexible guide member disposed within said wall thickness between said interior and exterior surfaces of said tube, said guide member extending in a substantially straight path parallel to and radially spaced from said axis and said guide member asymmetrical with respect to said axis, said guide member having a longitudinal dimension with a distal end extending to said distal end of said shaft;
      (c) said guide member fixed from movement relative to said tube; and
      (d) said guide member plastically deformable, at any one of a plurality of points along said longitudinal dimension of said guide member, when bent around a bending axis perpendicular to said longitudinal dimension beyond a bending limit with said bending axis perpendicular to and spaced from said longitudinal axis with said guide member and said tube defining a non-linear geometry at said bending axis to which said segment is biased in the absence of a deforming force on said segment.

2. A catheter according to claim 1 wherein said tube includes at least an inner layer having said interior surface and an outer layer having said exterior surface.

3. A catheter according to claim 1 wherein said guide member has a width and a thickness, said width measured perpendicular to a radial line from said axis to said longitudinal dimension of said guide member, said thickness measured perpendicular to both said longitudinal dimension and said width, said width being greater than said thickness.

4. A catheter according to claim 3 wherein said guide member is substantially rectangular in cross-section taken perpendicular to said longitudinal dimension.

5. A catheter according to claim 1 wherein said segment comprises:
   a second guide member which is substantially straight and flexible and disposed within said wall thickness between said interior and exterior surfaces of said tube;

said second guide member having a longitudinal dimension extending parallel to and radially spaced from said axis;

said second guide member plastically deformable when bent around a bending axis perpendicular to said longitudinal dimension beyond a bending limit; and said second guide member circumferentially spaced from said first guide member.

6. A catheter according to claim 1 further comprising a plurality of axially spaced-apart support rings surrounding said axis and contained within said wall thickness.

7. A catheter according to claim 1 further comprising a coil surrounding said axis and contained within said wall thickness.

8. A catheter according to claim 1 further comprising a woven support sleeve surrounding said axis and contained within said wall thickness.

9. A catheter according to claim 1 wherein said segment is positioned at a distal end of said catheter.

* * * * *